United States Patent [19]

Berg

[11] Patent Number: 5,160,412

[45] Date of Patent: Nov. 3, 1992

[54] DEHYDRATION OF ACETIC ACID BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 848,184

[22] Filed: Mar. 10, 1992

[51] Int. Cl.$^5$ .......................... B01D 3/36; C07C 51/46
[52] U.S. Cl. ...................................... 203/16; 203/60; 203/62; 203/63; 562/608
[58] Field of Search ....................... 203/16, 60, 62, 63; 562/608

[56] References Cited

U.S. PATENT DOCUMENTS

| | | | |
|---|---|---|---|
| 1,839,932 | 1/1932 | Ricard et al. | 203/60 |
| 2,028,800 | 1/1936 | Othmer | 203/16 |
| 2,033,978 | 3/1936 | Dreyfus | 203/63 |
| 2,049,441 | 8/1936 | Gordon | 203/16 |
| 2,159,146 | 5/1939 | Guinot | 203/16 |

*Primary Examiner*—Wilbur Bascomb, Jr.

[57] ABSTRACT

Acetic acid is difficult to separate from water by conventional distillation or rectification because of the close proximity of their boiling points. Acetic acid can be readily separated from water by using azeotropic distillation. Typical examples of effective agents are ethyl n-valerate and 4-methyl-2-pentanone.

1 Claim, No Drawings

DEHYDRATION OF ACETIC ACID BY AZEOTROPIC DISTILLATION

FIELD OF THE INVENTION

This invention relates to a method for separating acetic acid from water using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

Currently there are at least four commercial ways to manufacture acetic acid. The fermentation of fruit (apples) or wood waste are the oldest. The reaction of acetylene with water to form acetaldehyde followed by air oxidation is still in use. Fermentation of ethanol to acetic acid is used when cheap ethanol is available. The reaction of methanol with carbon monoxide in aqueous solution is currently in favor because of cheap methanol. The air oxidation of butane to give a multitude of products, approximately forty, including acetic acid is currently attractive. All of these processes present the problem of separating water from acetic acid. Acetic acid boils at 118° C., water at 100° C. but although these two do not form an azeotrope, they are far from being an ideal mixture. The separation of water from acetic acid by distillation becomes especially difficult at high concentrations of acetic acid.

S. S. Levush et. al. used ethyl acetate as the agent to separate water from acetic acid by azeotropic distillation, J. W. Troeger et.al. used n-propyl acetate, D. D. Lindley et.al. used n-methyl pyrrolidinone, T. W. Mix used trichlorotrifluoromethane and A. Serdyuk et.al. used cyclohexane as the azeotrope forming agent for this separation.

The advantage of using azeotropic distillation in this separation can be seen from the data shown in Table 1. If an agent can be found that will increase the relative volatility to 2.0, only 12 actual plates are required for 95% purity, with 2.7, only nine actual plates are required.

TABLE 1

Theoretical and Actual Plates Required vs. Relative Volatility for Acetic Acid - Water Separation

| Relative Volatility | Theoretical Plates Required At Total Reflux, 95% Purity | Actual Plates Required, 75% Eff. |
| --- | --- | --- |
| 1.12 | 52 | 70 |
| 1.20 | 33 | 44 |
| 1.25 | 27 | 36 |
| 1.30 | 23 | 31 |
| 1.35 | 20 | 27 |
| 1.40 | 18 | 24 |
| 2.0 | 9 | 12 |
| 2.7 | 7 | 9 |

OBJECTIVE OF THE INVENTION

The objects of this invention are to provide a process or method of azeotropic distillation that will enhance the relative volatility of water to acetic acid in their separation in a rectification column. It is a further object of this invention to identify certain organic compounds that are stable, can be readily separated from water and can be recycled to the azeotropic distillation column with little decomposition.

SUMMARY OF THE INVENTION

The objects of the invention are provided by a process for the separation of water from acetic acid which entails the use of certain organic compounds as the agent in azeotropic distillation.

DETAILED DESCRIPTION OF THE INVENTION

I have discovered that certain organic compounds will effectively increase the relative volatility between water and acetic acid by rectification when employed as the agent in azeotropic distillation. Table 2 summarizes the data obtained with these agents in a rectification column. The agents which are effective are methyl propionate, benzyl acetate, isopropyl acetate, amyl acetate, 2-methyl hexanone-5, 2-heptanone, diisobutyl ketone, 2-octanone, 4-methyl-2-pentanone, diethyl malonate, butyl ether, anisole, 2-undecanone, 2,4-pentanedione, propiophenone, isobutyl acetate, 4-methyl pentyl acetate, hexyl acetate, ethyl n-valerate, hexyl formate, amyl propionate, propyl caproate, hexyl ether, ethylene glycol diacetate, triacetin and isophorone.

TABLE 2

Data From Runs Made In Rectification Column

| Azeo. Former | Azeo. Water | Comp., Wt. % Agent | Wt. % Water | Overhead HAc | Wt. % Water | Stillpot HAc | Relative Volatility |
| --- | --- | --- | --- | --- | --- | --- | --- |
| Me propionate | 9 | 91 | 92.8 | 7.2 | 58.2 | 41.8 | 1.36 |
| Benzyl acetate | 75 | 25 | 97.8 | 2.2 | 81 | 19 | 1.35 |
| Isopropyl acetate | 20 | 80 | 93.6 | 6.4 | 39.8 | 60.2 | 1.5 |
| Amyl acetate | 33 | 67 | 99.5 | 0.5 | 58.5 | 41.5 | 1.9 |
| 2-Me-hexanone-5 | 45 | 55 | 99.6 | 0.4 | 62.7 | 37.3 | 2.0 |
| 2-Heptanone | 50 | 50 | 99.5 | 0.5 | 62.1 | 37.9 | 1.9 |
| Diisobutyl ketone | 55 | 45 | 99.5 | 0.5 | 67 | 33 | 1.9 |
| 2-Octanone | 70 | 30 | 99.1 | 0.9 | 70.7 | 29.3 | 1.9 |
| 4-Me-2-pentanone | 25 | 75 | 99.99 | 0.01 | 58.2 | 41.8 | 2.4 |
| Diethyl malonate | 20 | 80 | 99.5 | 0.5 | 52.7 | 47.3 | 2.0 |
| Butyl ether | 40 | 60 | 99.7 | 0.3 | 67 | 33 | 2.0 |
| Anisole | 40 | 60 | 99.7 | 0.3 | 73.3 | 26.7 | 1.7 |

TABLE 2-continued
Data From Runs Made In Rectification Column

| Azeo. Former | Azeo. Water | Comp., Wt. % Agent | Wt. % Water | Overhead HAc | Wt. % Water | Stillpot HAc | Relative Volatility |
|---|---|---|---|---|---|---|---|
| 2-Undecanone | 45 | 55 | 99.6 | 0.4 | 70 | 30 | 1.9 |
| 2,4-Pentanedione | 50 | 50 | 99.3 | 0.7 | 71 | 29 | 1.75 |
| Propiophenone | 5 | 95 | 89.7 | 10.3 | 68 | 32 | 1.2 |
| Isobutyl acetate | 28 | 72 | 99.9 | 0.1 | 49 | 51 | 2.1 |
| 4-Me pentyl acetate | 28 | 72 | 99.9 | 0.1 | 49 | 51 | 1.9 |
| Hexyl acetate | 58 | 42 | 99.2 | 0.8 | 78 | 22 | 1.6 |
| Et n-valerate | 44 | 56 | 99.8 | 0.2 | 59 | 41 | 2.7 |
| Hexyl formate | 46 | 54 | 99.9 | 0.1 | 61 | 39 | 1.6 |
| Amyl propionate | 50 | 50 | 99.8 | 0.2 | 67 | 33 | 2.1 |
| Propyl caproate | 67 | 33 | 97.2 | 2.8 | 67 | 33 | 1.4 |
| Hexyl ether | 73 | 27 | 99.8 | 0.2 | 57 | 43 | 1.4 |
| Et glycol diacetate | 85 | 15 | 95.6 | 4.4 | 61 | 39 | 1.4 |
| Triacetin | 88 | 12 | 93.4 | 6.6 | 56 | 44 | 1.4 |
| Isophorone | 75 | 25 | 99.1 | 0.9 | 71 | 29 | 1.7 |

THE USEFULNESS OF THE INVENTION

The usefulness or utility of this invention can be demonstrated by referring to the data presented in Tables 1 and 2. All of the successful agents show that water can be separated from acetic acid by means of azeotropic distillation in a rectification column and that the ease of separation as measured by relative volatility is considerable.

WORKING EXAMPLES

EXAMPLE 1

150 grams of acetic acid, 150 grams of water and fifty grams of ethyl n-valerate were charged to a glass perforated plate rectification column containing 7.3 theoretical plates. After five hours at total reflux, overhead and bottoms samples were taken and analysed by gas chromatography. The overhead was 99.8% water, 0.2% acetic acid; the bottoms was 59% water, 41% acetic acid which is a relative volatility of 2.7.

EXAMPLE 2

150 grams of acetic acid, 150 grams of water and fifty grams of 4-methyl-2-pentanone were charged to the glass perforated plate rectification column containing 7.3 theoretical plates. After six hours at total reflux, the overhead analysis was 99.9% water, 0.1% acetic acid; the bottoms analysis was 58.2% water, 41.8% acetic acid which is a relative volatility of 2.4.

I claim:

1. A method for recovering water from a mixture of water and acetic acid which comprises distilling a mixture of water and acetic acid in the presence of an azeotropic forming agent, recovering the water and the azeotrope forming agent as overhead product and obtaining the acetic acid from the stillpot, wherein said azeotrope forming agent comprises a material selected from the group consisting of methyl propionate, hexyl acetate, 2-methyl hexanone-5, diisobutyl ketone, hexyl formate, 2-octanone, 4-methyl-2-pentanone, diethyl malonate, 2-undecanone, 2,4-pentanedione, propiophenone, 4-methyl pentyl acetate, ethyl n-valerate, amyl propionate, propyl caproate, ethylene glycol diacetate, triacetin and isophorone.

* * * * *